United States Patent [19]

Adib

[11] Patent Number: 4,765,345
[45] Date of Patent: Aug. 23, 1988

[54] MAGNETIC SENSOR FOR JAW TRACKING DEVICE

[75] Inventor: Fray Adib, Seattle, Wash.

[73] Assignee: Myo-Tronics Research, Inc., Seattle, Wash.

[21] Appl. No.: 15,918

[22] Filed: Feb. 18, 1987

[51] Int. Cl.⁴ .............................................. A61B 5/10
[52] U.S. Cl. ..................................... 128/777; 433/69
[58] Field of Search ................. 128/1.4, 1.5, 723, 774, 128/777, 782; 33/179.5 R; 433/68, 69; 310/68 R; 318/254; 323/357; 324/219, 220, 234–236, 251, 260

[56] References Cited

U.S. PATENT DOCUMENTS

| 3,822,694 | 7/1974 | Mills . | |
|---|---|---|---|
| 4,197,855 | 4/1980 | Lewin | 128/782 |
| 4,303,077 | 12/1981 | Lewin et al. . | |
| 4,339,875 | 7/1982 | Muller | 310/68 R |
| 4,342,086 | 7/1982 | Adib . | |
| 4,383,535 | 5/1983 | Schorr . | |
| 4,386,405 | 5/1983 | Lewin et al. | 433/69 |
| 4,692,703 | 9/1987 | Extance et al. | 324/251 |

FOREIGN PATENT DOCUMENTS

| 84108496.5 | 5/1985 | European Pat. Off. . | |
|---|---|---|---|
| 2154731 | 9/1985 | United Kingdom | 433/68 |

*Primary Examiner*—Max Hindenburg
*Attorney, Agent, or Firm*—Christensen, O'Connor, Johnson & Kindness

[57] ABSTRACT

A magnetic field sensor for use in a jaw tracking device. The sensor includes a Hall effect generator (110) and a pair of flux concentrators (112, 114). The Hall effect generator has first (116) and second (118) sensing faces disposed on opposite sides of the generator. Each flux concentrator comprises a strip of concentrator material formed into a U-shape, with a pair of opposed, mutually parallel side members (120, 122, 130, 132) interconnected at one end by a cross member (124, 134). The generator and flux concentrators are positioned such that the cross members are adjacent and parallel to the respective sensing faces, with the side members extending away from one another in a direction normal to the sensing faces. The sensor also preferably includes a metal-filled adhesive (140) having a high thermal conductivity bonding each cross member to its respective sensing face.

6 Claims, 3 Drawing Sheets

MAGNETIC SENSOR FOR JAW TRACKING DEVICE

FIELD OF THE INVENTION

The present invention relates to dental diagnostic instruments and, in particular, to a jaw tracking device for providing information relating to movement of a patient's mandible.

BACKGROUND OF THE INVENTION

A jaw tracking device is a diagnostic dental instrument used for displaying and/or recording the movement of a patient's lower jaw and mandible. In a typical arrangement, a magnet is temporarily mounted beneath the lower lip of the patient. The jaw tracking device includes an array of magnetic sensors positioned on opposite sides of the patient's mandible. As the patient's mandible moves, the distance between the magnet and each of the sensors varies, and each sensor generates a corresponding electrical signal. The electrical signals from the sensors may be processed to produce data that indicates mandible movement in an anterior/posterior, lateral and/or vertical plane. Selected views of such data may be presented to an operator on the display screen of a monitor or oscilloscope. Typically, a jaw tracking device can also generate a waveform indicative of the vertical velocity of the mandible over time. A jaw tracking device can easily and quickly provide the kind of factual information needed to determine and diagnose an occlusal problem.

Although jaw tracking devices have been used with great success for many years, there are difficulties inherent with the use of magnetic sensors to track mandible movement. To increase accuracy and dynamic range, it is important that the sensors be as sensitive as possible to variations in the magnetic field caused by movement of the magnet with respect to the sensors. Because of the low-level nature of the signals produced by magnetic sensors, it is also important to minimize the effects that other parameters, such as temperature change, may have on the sensor output signals.

SUMMARY OF THE INVENTION

The present invention provides an improved magnetic field sensor for use in a jaw tracking device. In a preferred embodiment, the improved sensor comprises a Hall effect generator, a pair of flux concentrators, and means for mounting the generator and flux concentrators. The Hall effect generator has first and second sensing faces disposed on opposite sides of the generator. Each flux concentrator comprises a strip of concentrator material formed into a U-shape, with a pair of opposed, mutually parallel side members interconnected at one end by a cross member. The generator and flux concentrators are mounted such that the cross members are positioned adjacent and parallel to the respective sensing faces and such that the side members extend away from one another along a direction normal to the sensing faces. In a preferred embodiment, the sensor includes a metal-filled adhesive having a high thermal conductivity bonding each cross member to its respective sensing face.

DETAILED DESCRIPTION OF THE INVENTION

Figure 1:
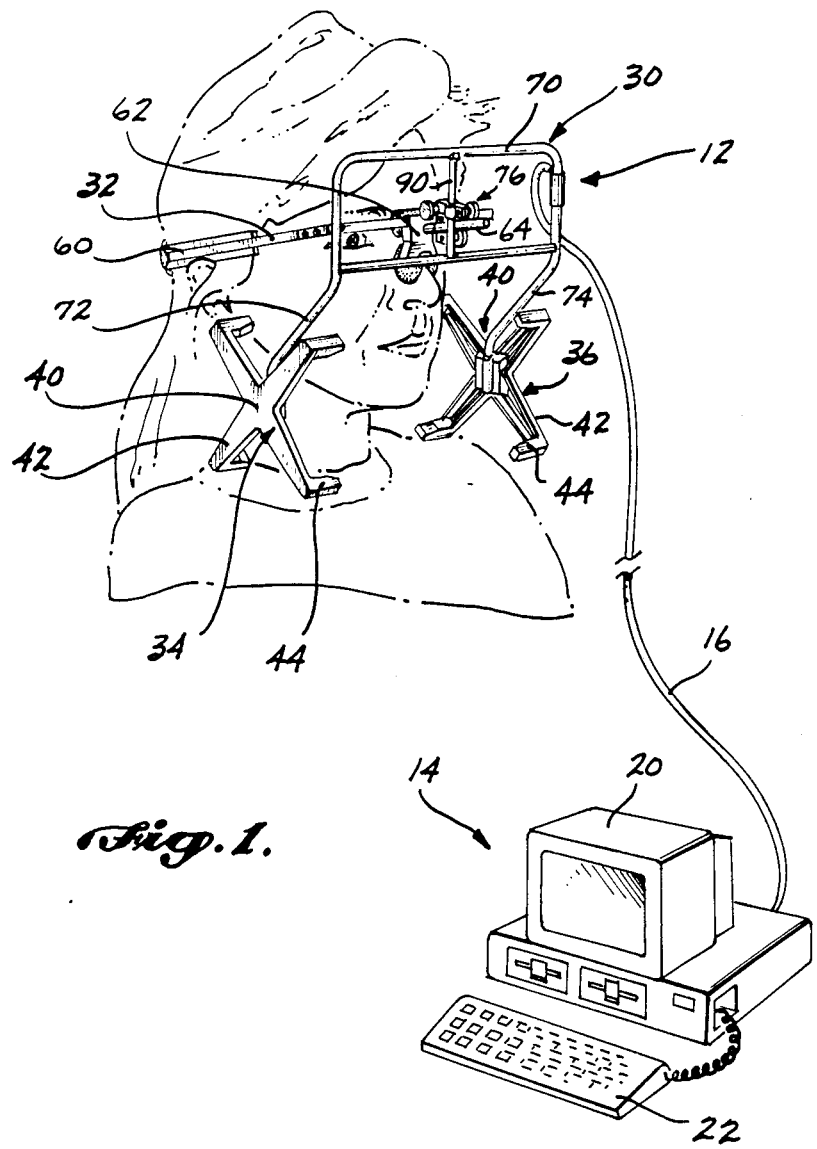
FIG. 1 is a perspective view of a jaw tracking device with which the magnetic sensor of the present invention may be used.

FIG. 1 illustrates a jaw tracking device in which the improved magnetic sensor of the present invention may be used. The jaw tracking device includes headpiece 12 mountable on the patient's head, and operator console 14 coupled to the headpiece via cable 16. In the illustrated embodiment, console 14 comprises a microcomputer that includes monitor 20 and keyboard 22. In general, the console may comprise any suitable device, such as a computer or a processor in combination with an oscilloscope, for processing the sensor signals and providing information relating to mandible movement.

Headpiece 12 comprises frame 30, mounting system 32 and identical sensor arrays 34 and 36. Mounting system 32 includes strap 60, fasteners 61 (only one fastener shown), nosepiece 62 and mounting pin 64. The fasteners are adjustably connected to one another, and pass around the patient's head for securing the frame to the patient. Nosepiece 62 is connected to strap 60, and rests on the patient's nose to support the principal weight of the headpiece. Mounting pin 64 extends in a forward direction from nosepiece 62, and comprises a cylindrical pin that comprises the single point of support of the frame. The frame includes vertical crosspiece 90 that is adjustably connected to mounting pin 64 by coupler 76.

Each sensor array comprises central hub area 40, four arms 42 extending outwardly from hub area 40, and magnetic sensors 44 located at the outer end of each arm, each sensor extending in an inward direction from the outer end of the arm towards the other sensor array. The arms are formed as pairs that extend in opposite directions from one another from the hub area. In the illustrated embodiment, there are a total of four arms and four sensors in each sensor array, and adjacent arms on a single sensor array are rotated 90 degrees with respect to one another.

Each magnetic sensor 44 preferably comprises a Hall effect sensor that has a sensing axis that is parallel to the elongated dimension of the sensor and normal to the plane in which arms 42 lie. Sensor arrays 34 and 36 are mounted to frame 30 such that the sensor arrays are bilaterally symmetric with respect to the patient's mandible. In particular, each magnetic sensor 44 is positioned directly across from an identical sensor on the opposite side of the patient's mandible.

Figure 2:
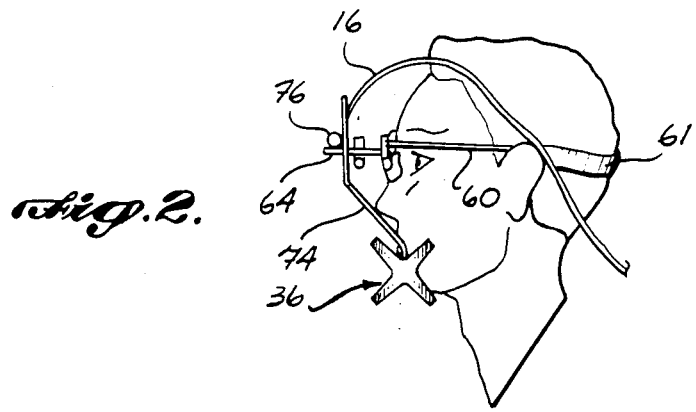
FIG. 2 is a side elevational view of the headpiece in use on a patient.
Figure 3:
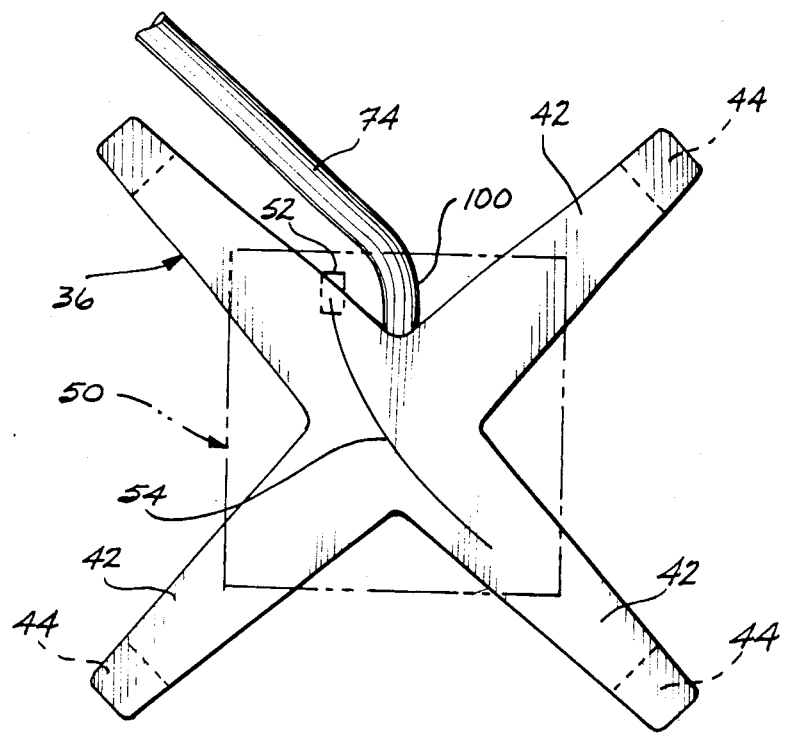
FIG. 3 is a side elevational view of one of the sensor arrays showing the detection zone.

Referring now to FIGS. 2 and 3, the eight sensors 44 operate to define a detection zone 50 that has a square cross section (as shown) and that occupies a volume that is centered between sensor arrays 34 and 36. The detection zone is the space in which there is a substantially linear relationship between the signals derivable from the sensor signals and the position of a magnet in the detection zone. To operate the jaw tracking device, a small magnet 52 is temporarily mounted beneath the lower lip of the patient. A principal function of headpiece 12 is to position sensor arrays 34 and 36 such that when the patient's lower jaw is raised (mouth closed), magnet 52 is positioned approximately as shown in FIG. 3 with respect to detection zone 50. Thereafter, movement of the patient's jaw will typically cause magnet 52 to follow a path such as path 54 shown in FIG. 3, and path 54 will remain within detection zone 50 throughout the range of mandible movement. The entire range of movement of the patient's mandible can thereby be accurately monitored by means of the jaw tracking device. Coupler 76 permits adjustment of the position of the frame with respect to the mounting system in both the posterior/anterior and vertical directions, and permits rotation of the frame with respect to the mounting system about a lateral axis. By such adjustments, the sensor arrays can be positioned as indicated in FIG. 3, such that the magnet is always within the detection zone.

Figure 5:
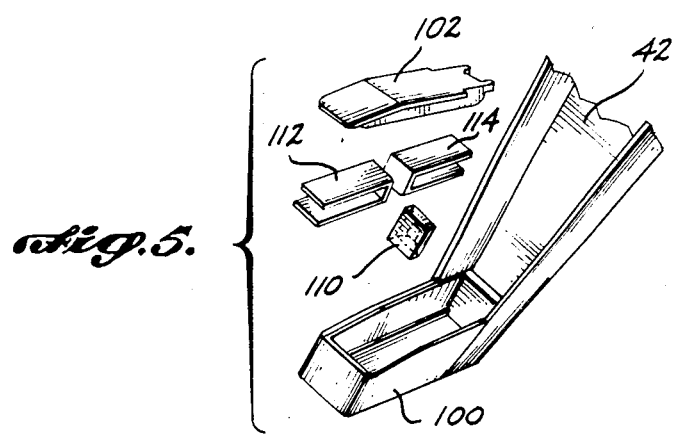
FIG. 5 is an exploded perspective view of the magnetic sensor of the present invention.
Figure 4:
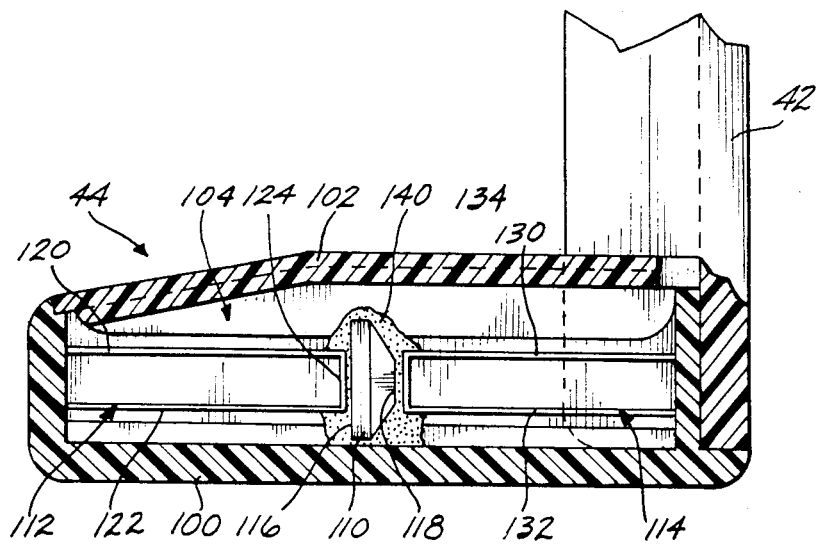
FIG. 4 is a cross-sectional view of the magnetic sensor of the present invention.

The construction of each magnetic sensor 44 is illustrated in greater detail in FIGS. 4 and 5. Each sensor includes an enclosure comprising housing 100 and panel 102 that is shaped to mate with housing 100 to form an elongated enclosed area 104 that has an approximately rectangular cross section. Within enclosure 104 are positioned Hall effect generator 110 and flux concentrators 112 and 114. In general, Hall effect generaor 110 should be as small and sensitive as possible. A suitable generator is the model BH-702 single axis Hall generator available from F. W. Bell. This generator has a generally truncated pyramid shape, as shown in FIG. 4, with a comparatively large face 116 at one end of the generator, and a comparatively small face 118 at the opposite end of the generator that includes a ferrite concentrator. Electrical leads (not shown) connect Hall effect generator 110 to the operator console via arms 42, frame 30 and cable 16 (FIG. 1).

Each flux concentrator 112 and 114 comprises a sheet of suitable flux concentrator material formed into a U-shape. A suitable flux concentrator material is molypermalloy. Flux concentrator 112 includes side members 120 and 122 joined by cross member 124, and flux concentrator 114 includes side members 130 and 132 interconnected by cross member 134. Cross members 124 and 134 are adhesively secured to faces 116 and 118 of generator 110 by means of an adhesive 140 having a high thermal conductivity. Preferably, the adhesive comprises a metal-filled epoxy, i.e., an epoxy into which a metal powder has been mixed. A suitable adhesive is the STYCAST (R) 2850KT castable epoxy available from Emerson & Cuming. By using an adhesive having a high thermal conductivity, heat generated in the Hall effect generator can efficiently flow through the adhesive to the flux concentrators. The flux concentrators thereby act as heat sinks and heat radiators, helping to maintain the temperature of the generator constant. In particular, such an arrangement minimizes the temperature change of the generator between the time at which the jaw tracking device is first powered on and the time at which the generator has reached thermal equilibrium after the jaw tracking device has been on for an extended period of time.

The back-to-back, U-shaped concentrators 112 and 114 surrounding generator 110 provide a distinct improvement in performance as compared to conventional concentrator arrangements. In particular, the arrangements shown in FIGS. 4 and 5 permit the concentrators to be bound to the generator over significant areas, to promote temperature stability as described above. In addition, the illustrated arrangement provides for a maximum amount of concentrator material adjacent to the sensor, without causing the size of the sensor to become too large to accommodate the widest mandible expected during normal usage of the jaw tracking device. The described sensor therefore provides both high accuracy and high sensitivity as compared with prior arrangements.

While the preferred embodiments of the invention have been illustrated and described, it will be understood that variations will occur to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. A magnetic field sensor for use in a jaw tracking device to monitor motion of a patient's mandible, the sensor comprising:
    a Hall effect generator having first and second sensing faces disposed on opposite sides of the generator;
    a pair of flux concentrators, each flux concentrator comprising a strip of concentrator material formed into a U-shape with a pair of opposed, mutually parallel side members interconnected at one end by a cross member; and
    means for mounting the generator and flux concentrators such that the cross members are positioned adjacent and parallel to the respective sensing faces, and such that the side members extend away from one another along a direction normal to the sensing faces.

2. The sensor of claim 1, wherein the means for mounting the generator and flux concentrators comprises a metal-filled adhesive bonding each cross member to its respective sensing face.

3. The sensor of claim 2, wherein the cross members are positioned to not be in direct contact with the generator.

4. The sensor of claim 3, wherein the adhesive fills the space formed between the cross members and the generator.

5. The sensor of claim 1, wherein the pair of flux concentrators comprise a first flux concentrator and a second flux concentrator, and further wherein the side members of the first flux concentrator are positioned to be parallel to the side members of the second flux concentrators.

6. The sensor of claim 1, wherein the side members have lengths substantially greater than the lengths of the cross members.

* * * * *